US011234787B1

(12) United States Patent
Staats et al.

(10) Patent No.: US 11,234,787 B1
(45) Date of Patent: Feb. 1, 2022

(54) MANIFOLD FOR FILTERING MEDICAL WASTE BEING DRAWN UNDER VACUUM INTO A MEDICAL WASTE COLLECTION SYSTEM

(71) Applicant: Stryker Corporation, Kalamazoo, MI (US)

(72) Inventors: Andy Staats, Issaquah, WA (US); Brian MacLachlan, Norton Shores, MI (US); Grant Westphal, Delton, MI (US); Stephen J. Reasoner, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 17/194,771

(22) Filed: Mar. 8, 2021

Related U.S. Application Data

(63) Continuation of application No. 17/100,373, filed on Nov. 20, 2020.

(51) Int. Cl.
  *G06F 21/56* (2013.01)
  *G06F 8/53* (2018.01)
  (Continued)

(52) U.S. Cl.
  CPC .............. *A61B 50/30* (2016.02); *G06F 8/53* (2013.01); *G06F 21/31* (2013.01); *G06F 21/562* (2013.01);
  (Continued)

(58) Field of Classification Search
  CPC . G06F 21/56; G06F 21/62; G06F 8/53; G06F 21/31; G06F 21/51; G06F 21/562;
  (Continued)

(56) References Cited

U.S. PATENT DOCUMENTS 3,808,634 A   5/1974 Szabo
4,802,198 A   1/1989 Guenther et al.
(Continued)

FOREIGN PATENT DOCUMENTS

CN   111741725 A   * 10/2020 ........... A61B 18/082

OTHER PUBLICATIONS

U.S. Appl. No. 17/100,377, filed Nov. 20, 2020.

*Primary Examiner* — Jayesh M Jhaveri
(74) *Attorney, Agent, or Firm* — Howard & Howard Attorneys PLLC

(57) ABSTRACT

A method of method of manufacturing a surgical waste collection manifold with a volume collected datum and a rover type to ensure compatibility with a surgical waste collection rover is provided. The surgical waste collection rover including a vacuum pump and a receiver defining an opening. The method includes obtaining a second manifold. The second manifold having a second housing defining a surface, the housing defining a second manifold volume and a second outlet opening in fluid communication with the second manifold volume. The method may further include coupling a second circuit to the surface of the second manifold, the second circuit comprising a second memory device including a third memory bank and a fourth memory bank, the third memory bank including a fifth memory field and the fourth memory bank including a sixth memory field. The method may further include programming the fifth memory field with an encrypted first hash digest based on the rover type and programming the sixth memory field with an encrypted second hash digest based on the volume collected datum.

10 Claims, 15 Drawing Sheets

(51) Int. Cl.
*G06F 21/31* (2013.01)
*G06F 21/62* (2013.01)
*G06F 21/70* (2013.01)
*A61B 50/30* (2016.01)
*A61M 1/00* (2006.01)
*G06F 21/51* (2013.01)

(52) U.S. Cl.
CPC ........ *G06F 21/563* (2013.01); *G06F 21/6245* (2013.01); *A61M 1/64* (2021.05); *A61M 1/79* (2021.05); *G06F 21/51* (2013.01); *G06F 21/70* (2013.01)

(58) Field of Classification Search
CPC .... G06F 21/563; G06F 21/6245; G06F 21/70; A61B 50/30
See application file for complete search history.

(56) References Cited

U.S. PATENT DOCUMENTS

| | | |
|---|---|---|
| 4,807,837 A | 2/1989 | Gawlik et al. |
| 4,905,944 A | 3/1990 | Jost et al. |
| 5,563,589 A | 10/1996 | Blaimont et al. |
| 5,941,182 A | 8/1999 | Greene |
| 5,974,500 A | 10/1999 | Maletsky et al. |
| 6,100,804 A | 8/2000 | Brady et al. |
| 6,318,636 B1 | 11/2001 | Reynolds et al. |
| 6,343,556 B1 | 2/2002 | Lanphear |
| 6,378,816 B1 | 4/2002 | Pfister |
| 6,607,170 B1 | 8/2003 | Hoftman |
| 6,861,954 B2 | 3/2005 | Levin |
| 6,883,439 B1 | 4/2005 | Moore |
| 6,892,052 B2 | 5/2005 | Kotola et al. |
| 7,171,890 B2 | 2/2007 | Oudelaar |
| 7,362,228 B2 | 4/2008 | Nycz et al. |
| 7,420,468 B2 | 9/2008 | Fabian et al. |
| 7,492,261 B2 | 2/2009 | Cambre et al. |
| 7,496,521 B1 | 2/2009 | Louie et al. |
| 7,541,933 B2 | 6/2009 | Volpi et al. |
| 7,557,711 B2 | 7/2009 | Volpi et al. |
| 7,594,668 B2 | 9/2009 | Arceta et al. |
| 7,617,137 B2 | 11/2009 | Kreiner et al. |
| 7,633,392 B2 | 12/2009 | Neuwirth |
| 7,643,798 B2 | 1/2010 | Ljung |
| 7,703,674 B2 | 4/2010 | Stewart et al. |
| 8,063,760 B2 | 11/2011 | Volpi et al. |
| 8,074,815 B2 | 12/2011 | Gerstner |
| 8,172,255 B1 | 5/2012 | Martin |
| 8,215,650 B2 | 7/2012 | Arceta et al. |
| 8,245,652 B2 | 8/2012 | Hung |
| 8,279,069 B2 | 10/2012 | Sawyer |
| 8,284,059 B2 | 10/2012 | Ross |
| 8,296,852 B2 | 10/2012 | Friedrich |
| 8,365,310 B2 | 1/2013 | Shamir |
| 8,446,245 B2 | 5/2013 | Wang et al. |
| 8,448,907 B2 | 5/2013 | Witschen |
| 8,545,416 B1 | 10/2013 | Kayyali et al. |
| 8,662,605 B2 | 3/2014 | McRorie et al. |
| 8,689,704 B2 | 4/2014 | Hodges et al. |
| 8,692,140 B1 | 4/2014 | Pollock et al. |
| 8,750,796 B2 | 6/2014 | Claus et al. |
| 8,768,251 B2 | 7/2014 | Claus et al. |
| 8,774,713 B2 | 7/2014 | Rose et al. |
| 8,789,156 B2 | 7/2014 | Fisk et al. |
| 8,831,509 B2 | 9/2014 | Moosavi et al. |
| 8,896,420 B2 | 11/2014 | Chang et al. |
| 8,905,317 B1 | 12/2014 | Hsu et al. |
| 8,963,025 B2 | 2/2015 | Pollock et al. |
| 8,981,938 B2 | 3/2015 | Kazerouni |
| 8,996,393 B2 | 3/2015 | Sobie |
| 9,039,016 B2 | 5/2015 | Abernethy et al. |
| 9,226,686 B2 | 1/2016 | Blair |
| 9,347,817 B2 | 5/2016 | Pollock et al. |
| 9,355,350 B2 | 5/2016 | Hsu et al. |
| 9,366,746 B2 | 6/2016 | Kazerouni |
| 9,389,643 B1 | 7/2016 | Clark et al. |
| 9,418,249 B2 | 8/2016 | Thueringer et al. |
| 9,475,514 B2 | 10/2016 | Hardy et al. |
| 9,489,785 B2 | 11/2016 | Klammer et al. |
| 9,496,927 B1 | 11/2016 | Grinberg et al. |
| 9,507,981 B2 | 11/2016 | Dor et al. |
| 9,646,182 B2 | 5/2017 | Volpi et al. |
| 9,774,455 B2 | 9/2017 | Klammer et al. |
| 9,792,408 B2 | 10/2017 | Blair et al. |
| 9,814,540 B2 | 11/2017 | Blair et al. |
| 9,843,580 B2 | 12/2017 | Fairbanks et al. |
| 9,933,106 B2 | 4/2018 | Stark |
| 9,977,865 B1 | 5/2018 | LaBorde |
| 9,980,681 B2 | 5/2018 | LaBorde |
| 9,996,717 B2 | 6/2018 | Volpi et al. |
| 10,002,269 B2 | 6/2018 | Dor et al. |
| 10,043,592 B1 | 8/2018 | LaBorde |
| 10,076,284 B1 | 9/2018 | LaBorde |
| 10,117,722 B2 | 11/2018 | Sweeney |
| 10,187,742 B2 | 1/2019 | Dor et al. |
| 10,292,661 B1 | 5/2019 | LaBorde |
| 10,298,403 B2 | 5/2019 | Klammer et al. |
| 10,417,465 B2 | 9/2019 | Volpi et al. |
| 10,460,837 B1 | 10/2019 | LaBorde |
| 10,471,188 B1 | 11/2019 | Zollinger et al. |
| 10,482,293 B2 | 11/2019 | Volpi |
| 10,482,377 B1 | 11/2019 | LaBorde |
| 10,628,739 B1 | 4/2020 | LaBorde |
| 10,719,747 B2 | 7/2020 | Stewart et al. |
| 10,722,617 B2 | 7/2020 | Murray et al. |
| 10,758,649 B2 | 9/2020 | Smith et al. |
| 10,783,991 B1 | 9/2020 | LaBorde |
| 10,804,081 B2 | 10/2020 | Chhatre et al. |
| 10,899,021 B2 | 1/2021 | Robinson et al. |
| 2002/0143320 A1 | 10/2002 | Levin |
| 2003/0151511 A1 | 8/2003 | Duncan et al. |
| 2005/0171495 A1 | 8/2005 | Austin et al. |
| 2006/0187059 A1 | 8/2006 | Fabian et al. |
| 2007/0028549 A1 | 2/2007 | Henderson |
| 2008/0029416 A1 | 2/2008 | Paxton |
| 2008/0098212 A1* | 4/2008 | Helms ................ H04N 21/8193 713/155 |
| 2008/0252045 A1 | 10/2008 | Rossini et al. |
| 2009/0015116 A1 | 1/2009 | Arceta et al. |
| 2009/0096574 A1 | 4/2009 | Oberle |
| 2009/0201133 A1 | 8/2009 | Bruns |
| 2009/0267765 A1 | 10/2009 | Greene et al. |
| 2010/0022900 A1 | 1/2010 | Peterson et al. |
| 2010/0039220 A1 | 2/2010 | Davis |
| 2010/0057167 A1 | 3/2010 | Evers et al. |
| 2010/0303603 A1 | 12/2010 | Galante et al. |
| 2011/0004276 A1 | 1/2011 | Blair et al. |
| 2011/0148579 A1 | 6/2011 | Strzelczyk et al. |
| 2012/0024864 A1 | 2/2012 | Champ |
| 2013/0126682 A1 | 5/2013 | Tholkes et al. |
| 2014/0028444 A1 | 1/2014 | Volpi et al. |
| 2014/0077050 A1 | 3/2014 | Huang |
| 2014/0091910 A1 | 4/2014 | Volpi et al. |
| 2014/0148095 A1 | 5/2014 | Smith et al. |
| 2014/0360412 A1 | 12/2014 | Zaccai et al. |
| 2015/0162957 A1 | 6/2015 | Saghbini et al. |
| 2015/0297307 A1 | 10/2015 | Sweeney |
| 2015/0304478 A1 | 10/2015 | Kim et al. |
| 2016/0070942 A1 | 3/2016 | Dor et al. |
| 2016/0292980 A1 | 10/2016 | Kazerouni |
| 2017/0195308 A1 | 7/2017 | Marka et al. |
| 2017/0258547 A1 | 9/2017 | Karasina |
| 2018/0039753 A1 | 2/2018 | Blair et al. |
| 2018/0285704 A1 | 10/2018 | Stewart et al. |
| 2018/0333309 A1 | 11/2018 | Merritt et al. |
| 2018/0353256 A1 | 12/2018 | Stewart et al. |
| 2019/0217352 A1* | 7/2019 | Maness ................. B09B 3/0016 |
| 2020/0405403 A1* | 12/2020 | Shelton, IV ....... A61B 17/3462 |

* cited by examiner

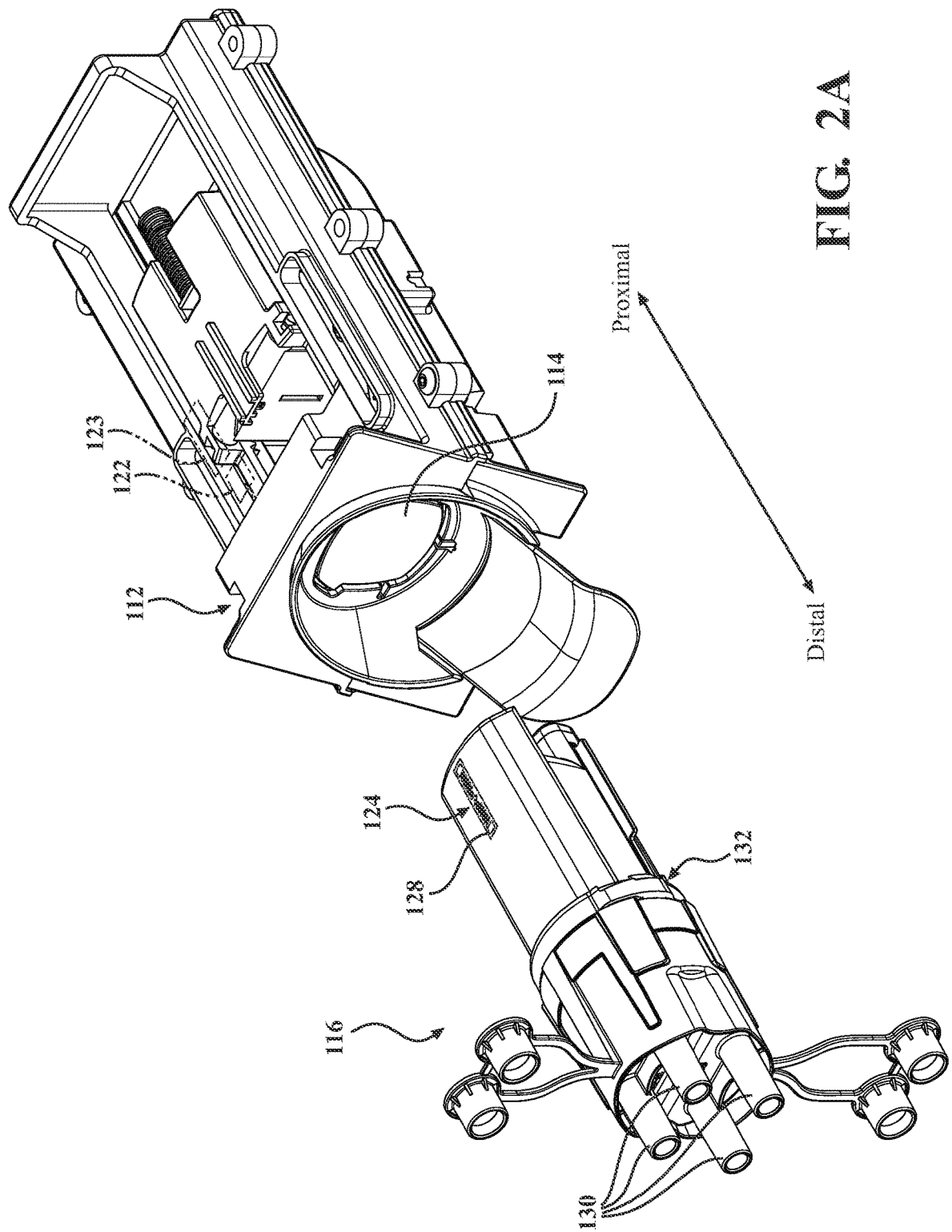

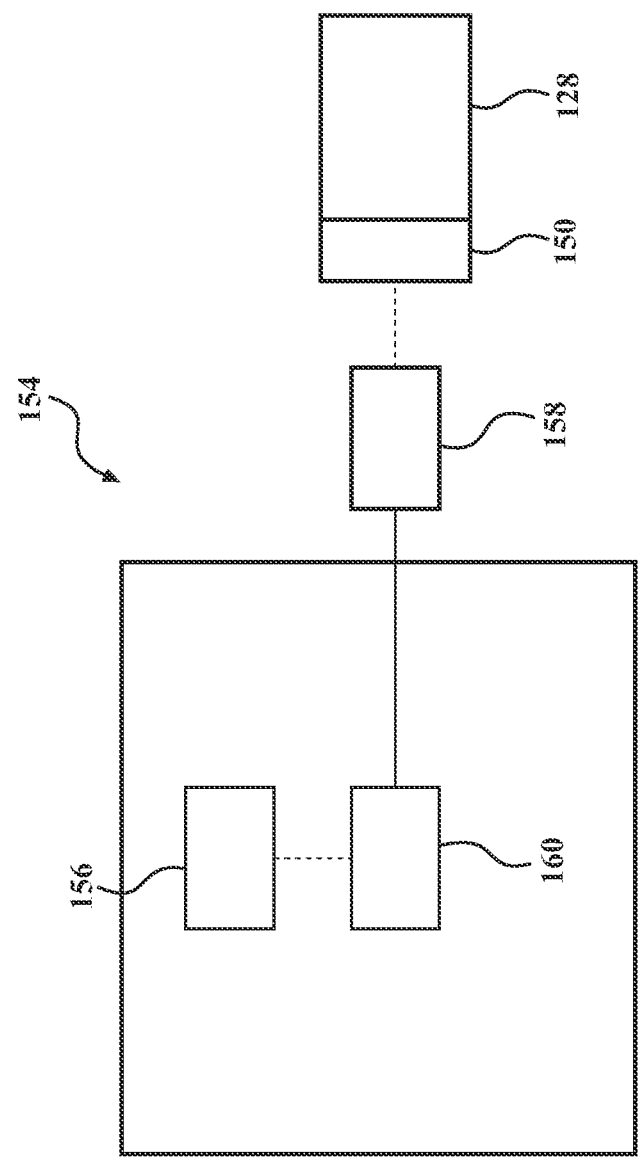

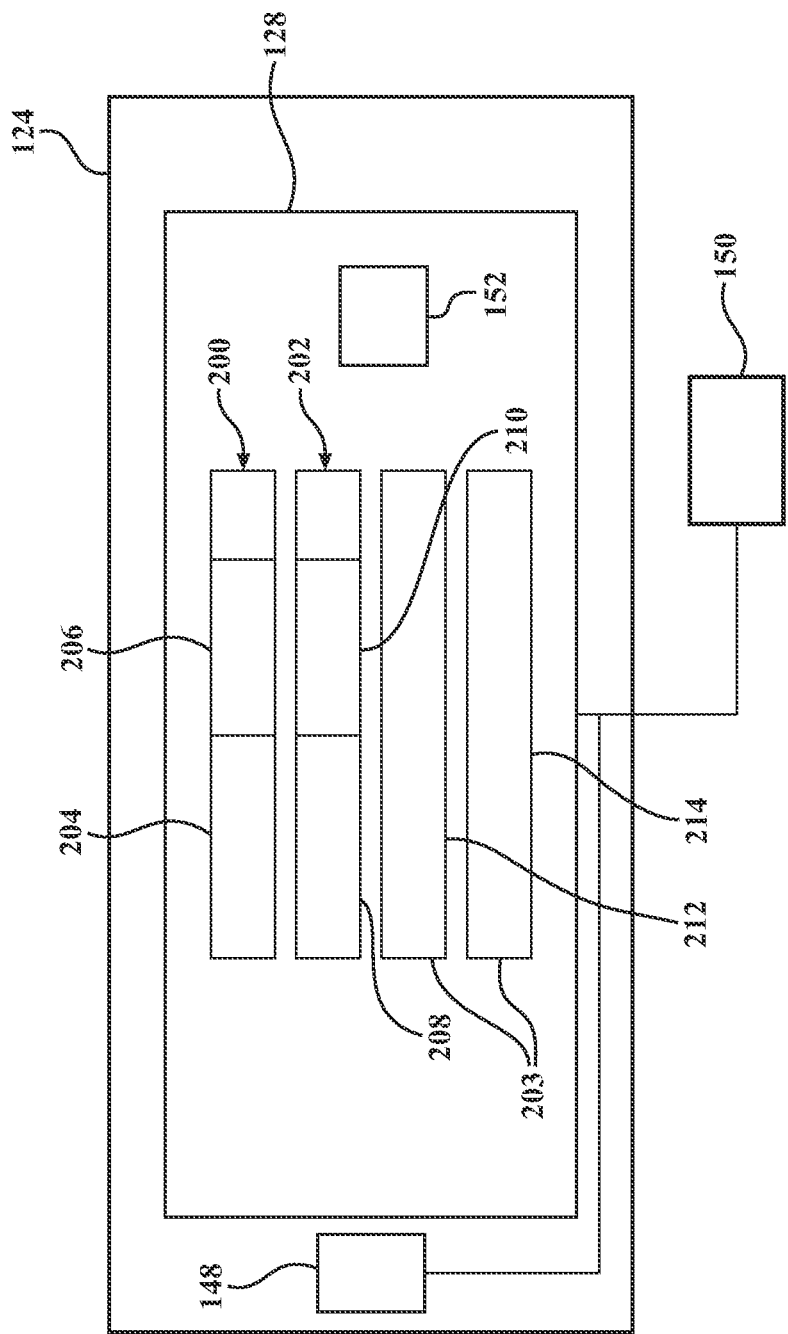

800

Obtain a first manifold comprising a first housing defining a surface, the first housing defining a first manifold volume and a first outlet opening in fluid communication with the first manifold volume
802

Couple a first circuit to the surface of the first housing, the first circuit comprising a second memory device including a first memory bank, the first memory bank including a first memory field and a second memory field
804

Extract object code from the first memory device
806

Disassemble at least a portion of the extracted object code into a comprehensible form having a different convention from the object code
808

Identify a fully compiled key call within the comprehensible form
810

Identify a static key call within the comprehensible form
812

Identify a first location for the fully compiled key call and a second location for the static key call
814

Start

Obtain a used first manifold comprising a first housing defining a surface, the first housing defining a first manifold volume and a first outlet opening in fluid communication with the first manifold volume, a first circuit coupled to the surface of the first housing and being used, the circuit comprising a first memory device including a first memory bank and a second memory bank, the first memory bank of the first circuit including a first memory field including a rover type and a second memory field including a first hash digest based on the rover type, the second memory bank including a third memory field including a volume collected datum, and a fourth memory field including a second hash digest based on the volume collected datum, the first circuit coupled to the surface of the manifold, the used first manifold including a contaminant in the first manifold volume and a time stamp field indicating a time of first use and a contamination bit indicative of prior vacuum
902

Program the second memory field of the used first manifold with a third hash digest, the third hash digest different from the first hash digest and being based on the rover type
904

Program the fourth memory field of the used first manifold with a fourth hash digest, the fourth hash digest different from the second hash digest and being based on the volume collected datum
906

Program a time stamp field on the first memory device indicating that no first use has occurred
908

Reset the contamination bit of the first circuit to be indicative of no prior vacuum
910
Remove the contaminant from the first manifold volume of the used first manifold to yield a cleaned first manifold.
912
FIG. 9B

MANIFOLD FOR FILTERING MEDICAL WASTE BEING DRAWN UNDER VACUUM INTO A MEDICAL WASTE COLLECTION SYSTEM

PRIORITY CLAIM

This is a continuation of copending U.S. application Ser. No. 17/100,373, filed Nov. 20, 2020, the entire contents of which is hereby incorporated by reference.

BACKGROUND

A byproduct of some surgical procedures is the generation of liquid, semisolid, and/or solid waste material. The liquid waste material may include bodily fluids and irrigating solution(s) at the surgical site, and the solid and semisolid waste material may include bits of tissue and pieces of surgical material(s). The medical waste, regardless of its phase, is preferably collected so it neither fouls the surgical site nor becomes a biohazard in the medical suite in which the procedure is being performed.

The medical waste may be removed from the surgical site through a suction tube under the influence of a vacuum provided by a suction source. One exemplary medical waste collection system is sold under the tradename NEPTUNE by Stryker Corporation (Kalamazoo, Mich.) with certain versions of the medical waste collection system disclosed in commonly owned United States Patent Publication No. 2005/0171495, published Aug. 4, 2005, International Publication No. WO 2007/070570, published Jun. 21, 2007, and International Publication No. WO 2014/066337, published May 1, 2014, the entire contents of each are incorporated herein by reference.

A manifold may be provided that facilitates interfacing the suction tube with the medical waste collection system. Additionally or alternatively, the manifold may include a filter element for filtering the waste material to avoid clogging or compromise of components of the medical waste collection system. The manifold may be single use and/or disposable. For example, an unused manifold may be operably coupled with the medical waste collection system before or during the procedure, and the used manifold may be operably decoupled from the medical waste collection system during or after the procedure. Facilitating safe and efficient repeated coupling and decoupling of manifolds with the medical waste collection system requires a robust interface, which remains an area of particular interest and development.

SUMMARY

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a method of harvesting an authentication procedure from a surgical waste collection unit. The method also includes obtaining a first manifold may include a first housing defining a surface, the first housing defining a first manifold volume and a first outlet opening in fluid communication with the first manifold volume; coupling a first circuit to the surface of the first housing, the first circuit may include a second memory device including a first memory bank, the first memory bank including a first memory field and a second memory field. The method also includes extracting object code from the first memory device; disassembling at least a portion of the extracted object code into a comprehensible form having a different. The method also includes convention from the object code; identifying a fully compiled key call within the comprehensible form, identifying a static key call within the comprehensible form, identifying a first location for the fully compiled key call and a second location for the static key call, determining an algorithm by which static key is incorporated into a fully compiled key based on the first location and the second location, compiling an imitation key using the determined algorithm that includes a static key call, encrypting a first hash digest based on a rover type using the imitation key, and programming the first memory field with the encrypted first hash digest. Other embodiments of this aspect include corresponding computer systems, apparatus, and computer programs recorded on one or more computer storage devices, each configured to perform the actions of the methods.

One general aspect includes a method of manufacturing a surgical waste collection manifold with a volume collected datum and a rover type to ensure compatibility with a surgical waste collection rover, the surgical waste collection rover including a vacuum pump and a receiver defining an opening. The method includes obtaining a used first manifold including a first housing defining a surface, the first housing defining a first manifold volume and a first outlet opening in fluid communication with the first manifold volume, a first circuit coupled to the surface of the first housing and being used, the circuit may include a first memory device including a first memory bank and a second memory bank, the first memory bank of the first circuit including a first memory field including a rover type and a second memory field including a first hash digest based on the rover type, the second memory bank including a third memory field including a volume collected datum, and a fourth memory field including a second hash digest based on the volume collected datum, the first circuit coupled to the surface of the manifold, the used first manifold including a contaminant in the first manifold volume and a time stamp field indicating a time of first use and a contamination bit indicative of prior vacuum. The method also includes programming the second memory field of the used first manifold with a third hash digest, the third hash digest different from the first hash digest and being based on the rover type. The method also includes programming the fourth memory field of the used first manifold with a fourth hash digest, the fourth hash digest different from the second hash digest and being based on the volume collected datum. The method also includes programming a time stamp field on the first memory device indicating that no first use has occurred. The method also includes resetting the contamination bit of the first circuit to be indicative of no prior vacuum. The method also includes removing the contaminant from the first manifold volume of the used first manifold to yield a cleaned first manifold. Other embodiments of this aspect include corresponding computer systems, apparatus, and computer programs recorded on one or more computer storage devices, each configured to perform the actions of the methods.

One general aspect includes a method of manufacturing a surgical waste collection manifold with a volume collected datum and a rover type to ensure compatibility with a surgical waste collection rover based on a first manifold having a first circuit. The method includes obtaining a second manifold may include a second housing defining a surface, the second housing defining a second manifold volume and a second outlet opening in fluid communication with the second manifold volume. The method also includes coupling a second circuit to the surface of the second housing, the second circuit may include a second memory device including a third memory bank and fourth memory bank, the third memory bank including a third memory field, and the fourth memory bank including a fourth memory field. The method also includes reading the encrypted first hash digest based on rover type and the encrypted second hash digest based on the volume collected datum from the first circuit. The method also includes programming the third memory field based on the reading of the encrypted first hash digest. The method also includes programming the fourth memory field based on the reading of the encrypted second hash digest. The method also includes reading a first randomized data set from the first circuit. The method also includes programming the second circuit with a second randomized data set based on the reading of the first randomized data set. Other embodiments of this aspect include corresponding computer systems, apparatus, and computer programs recorded on one or more computer storage devices, each configured to perform the actions of the methods.

BRIEF DESCRIPTION OF THE DRAWINGS

Advantages of the present disclosure will be readily appreciated as the same becomes better understood by reference to the following detailed description when considered in connection with the accompanying drawings.

FIG. 2A is a perspective view of the manifold and the receiver with the manifold oriented for insertion into an opening of the receiver.

FIG. 5 is a schematic view of a programming station and the first circuit of FIG. 2.

FIG. 6A is a schematic view of the first circuit of FIG. 2.

FIGS. 8A-8B are flow charts depicting an exemplary method.

FIGS. 9A-9B are flow charts depicting another exemplary method.

DETAILED DESCRIPTION

Figure 1:
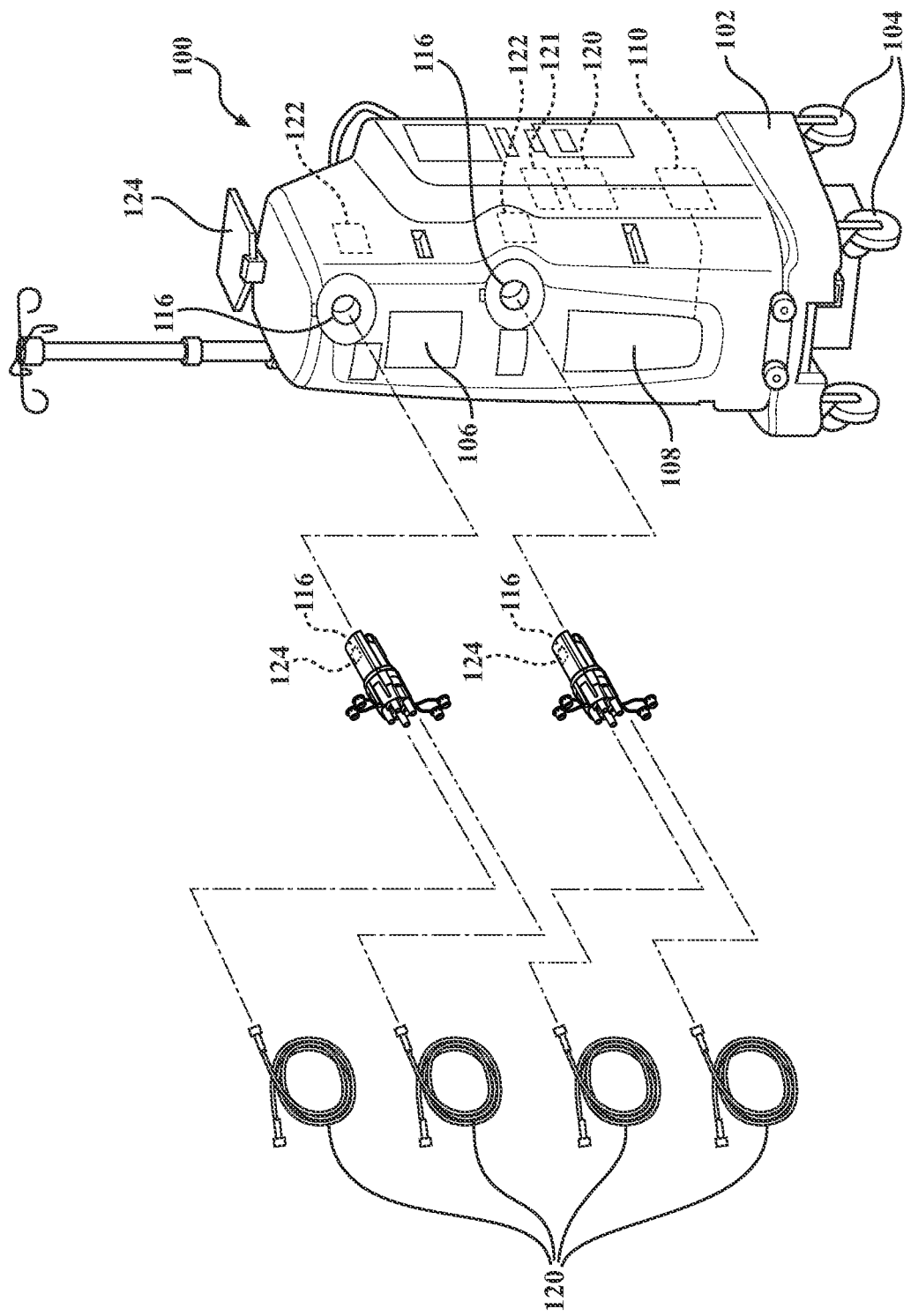
FIG. 1 is a perspective view of a medical waste collection system with each of two manifolds configured to be removably inserted into a respective one of two receivers of the medical waste collection system. Two suction tubes are configured to be removably coupled to each of the two manifolds.

FIGS. 1 and 2 show a waste collection unit 100, such as a surgical waste collection unit, for collecting the waste material generated during medical procedures; more particularly, surgical procedures. The waste collection unit 100 collects the waste material and/or stores the waste material until it is necessary or desired to off-load and dispose of the waste material. The waste collection unit 100 may be transported to and operably coupled with a docking station through which the waste material is emptied.

The waste collection unit 100 may include a base 102 and wheels 104 for moving the waste collection unit 100 along a floor surface within a medical facility. The waste collection unit 100 includes at least one waste container 106, 108 defining a waste volume for collecting and storing the waste material. FIG. 1 shows a first waste container 106 arranged above a second waste container 108 having a relatively greater or larger volume than the first waste container 106. A vacuum pump 110 (in phantom) is supported on the base 102 and configured to draw suction on one or both of the first and second waste containers 106, 108 through one or more vacuum lines. At least one vacuum regulator may also be supported on the base 102 and in fluid communication with the vacuum pump 110 and the waste container(s) 106, 108. The vacuum regulator(s) are configured to regulate a level of the suction drawn on the waste container(s) 106, 108. Suitable construction and operation of several subsystems of the waste collection unit 100 are disclosed in the aforementioned, commonly owned United States Patent Publication No. 2005/0171495, International Publication No. WO 2007/070570, and International Publication No. WO 2014/066337. Suitable construction and operation of several subsystems of the waste collection unit 100 may also be disclosed in commonly owned International Publication No. WO 2017/112684, published Jun. 29, 2017, the entire contents of which are hereby incorporated by reference.

The waste collection unit 100 includes at least one receiver 112 supported on the base 102. In a general sense, the receiver(s) 112 define an opening 114 dimensioned to removably receive at least a portion of a manifold 116, such as a surgical waste collection manifold, in a manner to be described throughout the present disclosure. FIG. 1 shows two receivers 112 with each of the receivers 112 associated with a respective one of the first and second waste containers 106, 108. Alternatively, a single receiver and/or a single manifold may be provided. The receiver(s) 112 include a suction inlet configured to be arranged in fluid communication with the respective one of the waste containers 106, 108. A suction path may be established from suction tube(s) 118 to the waste containers 106, 108 through the manifold(s) 116 removably inserted into the receiver(s) 112. The vacuum generated by the vacuum pump 110 is drawn on the suction tube(s) 118, and the waste material at the surgical site is drawn through the manifold(s) 116, through the suction inlet through a suction outlet of the receiver 112, and into the waste container(s) 106, 108.

The waste collection unit 100 may include a controller 120. The controller 120 may be in communication with the vacuum pump 110. The controller 120 may provide for overall control of the waste collection unit 100. The controller 120 may regulate the on/off operation of the vacuum pump 110. The controller 120 may also regulate the vacuum flow through the manifold 116.

A reader 122 may be positioned adjacent the receiver 112 to allow the waste collection unit 100 to communicate with a first circuit 124 positioned on or in the manifold 116 when the manifold 116 is inserted into the receiver 112. The first circuit 124 may be coupled to a surface, such as an internal or external surface of the manifold 116. The controller 120 may be in communication with the reader 122 through a reader controller 123.

The waste collection unit 100 includes a user interface 126 in operable communication with controller 120 that is configured to display operational data and provide audible tones to a user, and to accept user inputs. The user interface 126 may be a touchscreen display. Surgical personnel enter commands to regulate the waste collection unit 100 based on the pressing of button images presented on the user interface 126.

The controller 120 (or reader controller 123) instructs the reader 122 to repetitively emit a basic interrogation signal. If the manifold 116 is not fitted to the receiver 112, the manifold 116 does not emit a response to the basic interrogation signal. The controller 120 and reader 122 may cooperate to continually interrogate the manifold 116.

The controller 120 also inhibits activation of the vacuum pump 110 until the manifold 116 has been authenticated by the reader 122. This controller 120 may serve as a master override that prohibits the vacuum pump 110 from being actuated unless, as described below, an appropriate manifold 116 is fitted to the waste collection unit 100. If the user tries to actuate the vacuum pump 110 without a manifold 116 being authenticated, the controller 120 prevents activation of the vacuum pump. The system may also cause a warning message to be presented on the user interface 126.

Figure 2B:
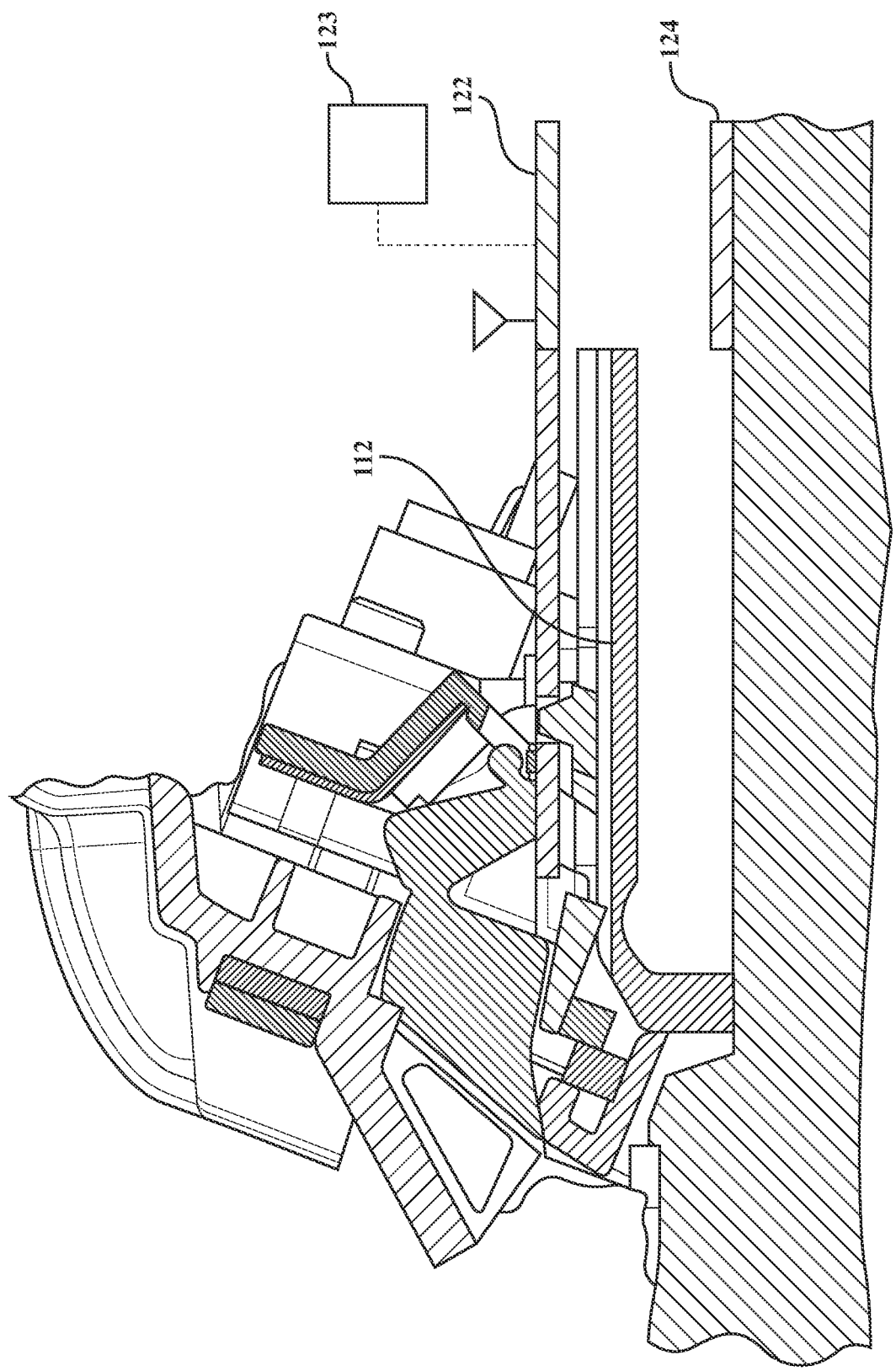
FIG. 2B is a schematic cross-sectional view of the manifold and the receiver, with the reader and the reader controller.

Referring to FIGS. 2A and 2B, a manifold 116 is configured to be seated in the receiver 112 and within range of the reader. Once this event occurs and when the reader sends an interrogation signal, the first circuit 124 sends a basic response to the reader 122. In this response, certain data in a memory device 128 of the first circuit 124 is forwarded through the reader 122 (and through the reader controller 123) to the controller 120. The controller 120 then performs an authentication procedure based on the certain data in the memory device 128 of the first circuit 124.

Referring to FIG. 2A, the manifold 116 is shown in a decoupled operative position in which the manifold 116 is separate or spaced apart from the receiver 112. FIG. 2A may be representative of the manifold 116 prior to insertion into the receiver 112 and/or after removal of the manifold 116 from the receiver 112. The manifold 116 is configured to be inserted into the receiver 112 through the opening 114, and the suction tube(s) 118 are coupled to inlet fitting(s) 130 of the manifold 116. The resulting arrangement is schematically reflected in FIG. 1, in which two suction tubes 118 are coupled to two of four inlet fittings 130 of each of the manifolds 116. Any number of inlet fitting(s) (130) are contemplated, and it is further contemplated that the suction tube(s) 118 may be integral with a housing 132 of the manifold. The aforementioned suction path is established, and an instrument (not shown) coupled to an end of the suction tube(s) 118 opposite the manifold(s) 116 may be directed to the surgical site to collect the waste material under the influence of the vacuum provided by the vacuum pump 110. In FIG. 2B, the manifold is shown in a coupled position and the first circuit 124 within range of the reader 122.

Figure 3:
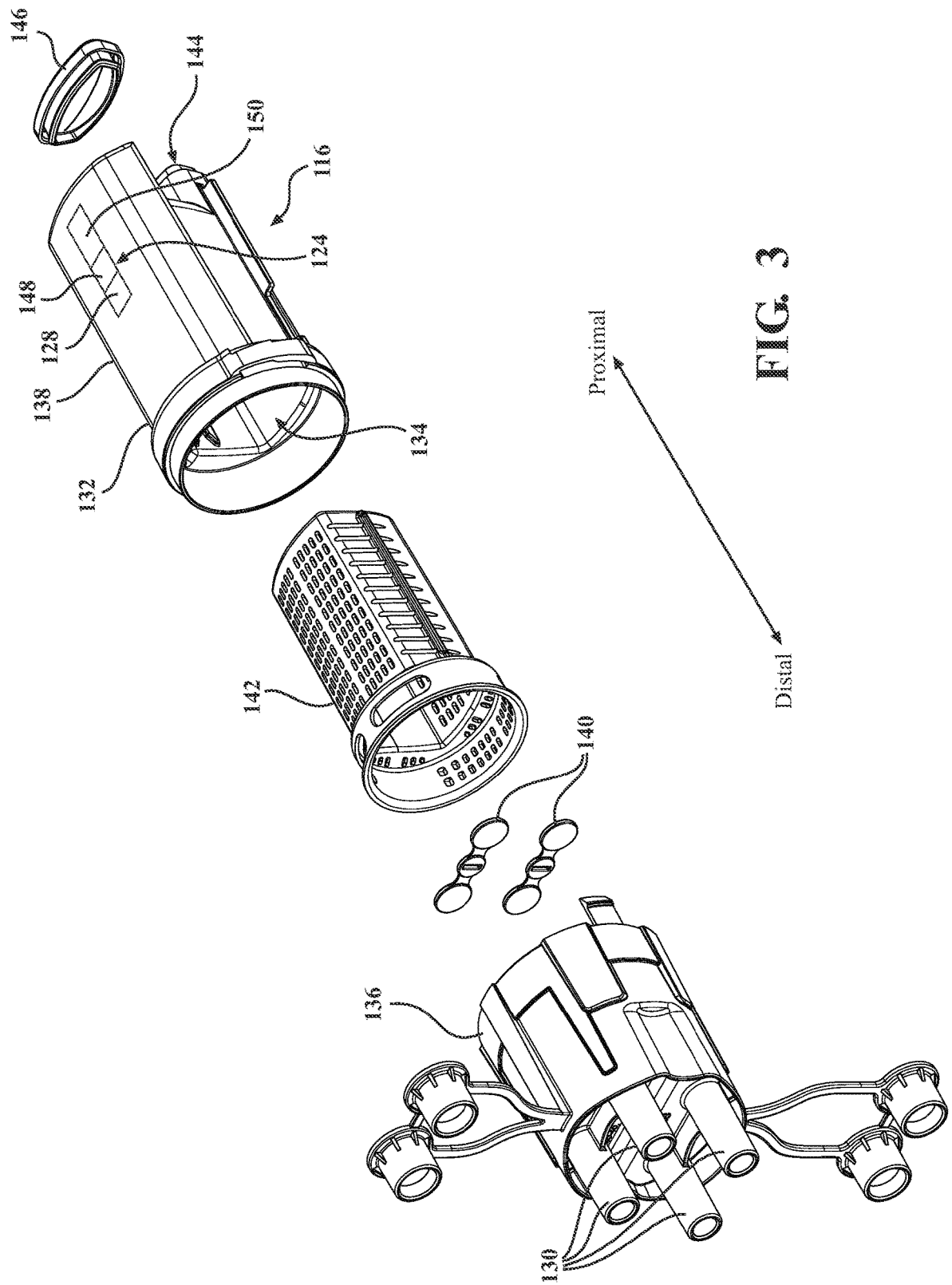
FIG. 3 is an exploded view of the manifold.

With further reference to FIGS. 2A-B and 3, the manifold 116 includes the housing 132. The housing 132 may define a manifold volume 134 in certain configurations. The housing 132 may be considered any external structure or component of the manifold 116, and more particularly any structure or component that at least partially defines the manifold volume 134. FIG. 2 shows the manifold 116 including a head 136 coupled to a trunk 138 to at least partially form the housing 132. The head 136 is positioned distal to the trunk 138 when the manifold 116 is oriented for insertion into the opening 114 of the receiver 112, as shown in FIG. 2. In an alternative to the multi-piece construction including the head 136 and the trunk 138, the housing 132 of the manifold 116 may be of unitary or monolithic construction. The head 136 (or any other portion of the housing 132) may include the inlet fitting(s) 130. The inlet fitting(s) 130 may define a distal end of the manifold 116. Alternatively, the inlet fitting(s) 130 may be coupled to a different structure separate from the housing 132 (i.e., not directly coupled to the head 136) with the inlet fitting(s) 130 being in fluid communication with an outlet opening 242 (to be described) to establish the suction path. It is further contemplated that any features described as being a part of the head 136 may alternatively be a part of the trunk 138, and any features described as being a part of the trunk 138 may alternatively be a part of the head 136.

Suitable materials for forming the housing 132 may include polymers, composites, metals, ceramics, and combinations thereof. The materials include sufficient anticorrosive properties to avoid degradation when exposed to the waste material and sufficient mechanical properties to maintain integrity under the vacuum levels to be provided by the waste collection unit 100. The polymers of polyethylene, polypropylene, polyvinyl chloride, polyethylene terephthalate (PET, PETE), polystyrene, polycarbonate, and poly (methyl methacrylate) may be particularly well suited for the manifold 116 in low-cost and disposable implementations. The manifold may be formed using an injection-molding process.

Figure 4:
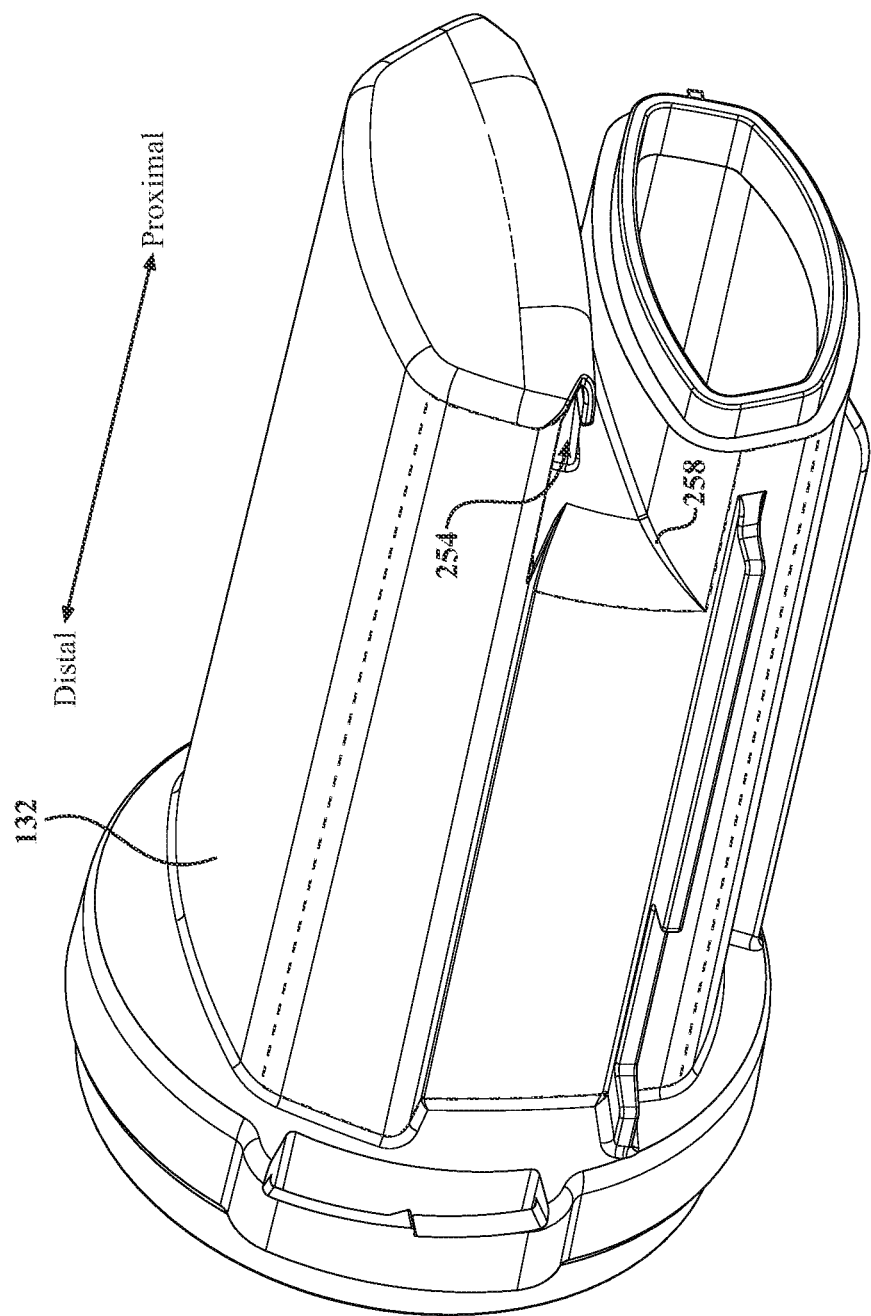
FIG. 4 is a perspective view of the proximal end of the manifold of FIG. 2.

Referring again to FIG. 4, the manifold 116 may include at least one valve 140 configured to prevent backflow from the manifold volume 134 through the inlet fittings 130. During assembly of the manifold 116, the valve(s) 140 may be coupled to the housing 132, and more particularly to the head 136. The sealing of the proximal end of the inlet fittings 130 prevent backflow from the manifold volume 134 through the inlet fittings 130, and thus possible egress of the waste material through the inlet fittings 130.

Referring now to FIG. 3, a filter element 142 may be disposed within the manifold volume 134. The filter element 142, in a broad sense, includes structures configured to capture or collect the semisolid or solid waste material entrained within the liquid waste material being drawn through the manifold 116 under the influence of the vacuum provided by the waste collection unit 100.

Referring again to FIG. 4, the housing 132 may define an outlet opening 144 that is in fluid communication with the manifold volume 134. Waste fluid may flow through the inlet fittings 130 into the manifold volume 134 and out through the outlet opening 144 into one or more of the first waste container 106 and the second waste container 108.

A drip seal 146 may be in sealing communication with the outlet opening 144 of the manifold 116. As to be described, the drip seal 146 may function to seal with a complementary sealing surface of an inlet mechanism including the suction inlet on the waste collection unit 100. The drip seal 146 may be of unitary or monolithic construction or be a multi-piece component. The drip seal 146 may be formed of a polymeric material with suitable hardness and resiliency, for example, a rubber or plastic having a Shore A Hardness within the range of approximately 20 to 90 durometers, and more particularly within the range of approximately 35 to 75 durometers, and even more particularly within the range of approximately 50 to 60 durometers.

Various other features of the manifold 116 and the waste collection unit 100 are contemplated. To that end, the disclosures of WO2019222655 and U.S. Pat. No. 10,471,188 are each incorporated by reference in their entirety.

The first circuit 124, including the memory device 128, may be coupled to an internal or external surface of the housing 132 of the manifold 116 and positioned to be detected by the reader 122 of the waste collection unit 100. Referring to FIG. 3, the first circuit 124 may be disposed on the upper wall of the housing 132. As previously mentioned, the upper wall may be generally horizontally-oriented when the manifold 116 is oriented for insertion into the receiver 112.

The first circuit 124 may be configured to be detected by the reader 122 when the manifold 116 is in various positions within the receiver 112. In particular, the first circuit 124 may be configured to be detected by the reader 122 when the manifold 116 is in the fully inserted operative position within the receiver 112. For example, the reader 122 may be positioned in the receiver 112 such that the first circuit 124 is only detectable when the manifold 116 is in the fully inserted operative position within the receiver 112 (i.e., is in fluid communication with the first waste container 106 and/or the second waste container 108). Should an article be incapable of being inserted to the fully inserted operative position for reasons previously described, no data communication is established between the first circuit 124 and the reader 122, and the controller 120 may prevent operation of the waste collection unit 100.

The first circuit 124 may include a manifold controller 148. The manifold controller 148 may be in communication with the memory device 128. Generally, the memory device 128 is useful for storing data for determining whether the manifold 116 is usable with the waste collection unit 100. The first circuit 124 may further include an antenna 150 to allow communication between the reader 122 and the memory device 128. In some configurations, the first circuit is compliant with the ISO 15693 RFID tag standard and therefore includes an absolutely (globally) unique 64-bit UID that is indelibly written during manufacture of the tag.

The memory device 128 may be NOVRAM or EEPROM. Alternatively, the memory device 128 may be any form of computer-readable media. Computer-readable media contained herein refers to a solid-state storage, or any available media that can be accessed by the manifold controller 148. That is, computer readable storage media includes non-transitory, volatile and non-volatile, removable and nonremovable media implemented in any method or technology for storage of information such as computer-readable instructions, data structures, program modules or other data. For example, computer-readable storage media includes RAM, ROM, EPROM, EEPROM, flash memory, other solid state memory technology, or any other medium which can be used to store the desired information, and which can be accessed by manifold controller 148.

The memory device 128 may include one or more one-time writable memory fields 152 that permit the changing of a memory value from zero to one or from one to zero only, and not vice versa. As an example, when new, the one-time writable memory field 152 has an initial value of one, or zero, or set or cleared. When the manifold 116 is used, a successive one of the bit values is set to zero (through a signal from the waste collection unit 100). In certain instances, if the waste collection unit 100 determines that the one-time writable memory field 152 is set to zero, upon initialization, the waste collection unit 100 reads the bit values and, being that all are zero, the waste collection unit 100 prevents usage of the manifold 116. Since the one-time writable memory field 152 cannot be rewritten to a value of one, there is no way to change the bit values to a value of one to allow additional uses.

Referring to FIG. 6A, the first circuit 124 may be further configured to set a manifold contamination bit in the one-time writable memory field 152 in response to a contamination command signal received from the waste collection unit 100. The contamination command signal may be sent by the controller 120 based on a determination by the controller 120 as to whether there has been vacuum pressure in the manifold 116 by monitoring whether or not the vacuum pump 110 was turned on and was set at a non-zero vacuum setting (indicative of prior vacuum). Alternatively, the first circuit may be programmed to send a contamination signal in response to receiving a contamination command signal. For example, the first circuit may be coupled to a processor that generates a contamination signal which emulates the response sought by the waste collection unit 100 without actually setting the contamination bit. It should be understood that the contamination bit may also have a condition before the vacuum pump has been turned on to a non-zero setting, which is indicative of no prior vacuum. The method may include resetting the contamination bit from a condition indicative that the prior vacuum has been applied to a condition that is indicative of no prior vacuum.

Referring to FIG. 5, a programming station 154 may be provided. The programming station 154 may include a programing station memory 156, a programming station transceiver 158, and a programming station processor 160 in communication with the programming station memory 156 and the programming station transceiver 158. The programming station memory 156 may include certain information needed for proper operation of the waste collection unit, including but not limited to a datum of the following types: volume collected datum; rover type; number of insertions permitted; and/or a maximum volume allowed usage limit. The programming station 154 may also include a set of programmable instructions for executing a method of preparing the first circuit 124 as described here, as well as the second circuits, etc.

Referring again to FIG. 6A, the memory device 128 may include one or more memory banks, such as a first memory bank 200 and a second memory bank 202. The term 'memory bank' may be a structural or logical distinction between portions of the memory device 128 of the first circuit 124.

The first memory bank 200 may include a first memory field 204 and a second memory field 206. The second memory bank 202 may include a third memory field 208 and a fourth memory field 210. Additional memory banks may be included. Certain memory fields described below may be in any memory bank without limitation.

In one example, the first memory field 204 is programmed with a rover type and the second memory field is programmed with a first hash digest based on the rover type. In addition, the third memory field may be programmed with a volume collected datum and the fourth memory field is programmed with a second hash digest based on the volume collected datum. As described below, the second hash digest may be in encrypted or decrypted form.

The rover type designates the type of waste collection unit for which the manifold 116 is suited. For example, it is contemplated that certain manifold designs are only usable with certain configurations of the waste collection unit, such as an obstetrics waste collection unit, an endoscopic waste collection unit, or a general surgery waste collection unit.

Alternatively, the rover type may designate a capacity of the waste collection unit, such as a 20 L unit, a 30 L unit, etc. The volume collected datum designates the amount of fluid that was channeled through the manifold in question into the one or more of the waste containers 106, 108. This ensures that the manifold 116 is not used beyond its expected functionality due to deterioration in the performance of one or more of the seals and/or valves of the manifold 116. This ensures that the manifold 116 and the waste collection unit 100 each performs as expected during the surgical/medical procedures.

The first memory bank 200 and/or the second memory bank 202 may include additional memory fields 203 beyond those specified above. Those memory fields may include additional datums that are readable by the waste collection unit 100 when the manifold 116 is inserted into the receiver 112. These include but are not limited to a number of insertions permitted; the number of insertions performed; and a maximum volume allowed. The number of insertions permitted is a number of times that a particular manifold can be inserted into a receiver before the waste collection unit triggers a response, such as by controlling the vacuum pump and/or a user interface to indicate that the number of actual insertions exceeds the number of insertions permitted. The number of insertions performed tracks the number of times that a particular manifold has been inserted into a receiver. This datum can be compared to the number of insertions permitted, and the outcome of that comparison can be used to trigger a response by the waste collection unit 100. The maximum volume allowed usage limit designates the amount of fluid than can be channeled through the manifold in question into the one or more collection tanks before the waste collection unit triggers a response, such as by controlling the vacuum pump and/or a user interface to indicate that the amount channeled exceeds a the maximum volume allowed usage limit.

The first circuit 124 may include one or more memory fields including an identifier datum. The identifier datum may include a UID having a bit string length of 64 bits. In some configurations, the first circuit 124 is compliant with the ISO 15693 RFID tag standard and therefore includes an absolutely (globally) unique 64-bit UID that is indelibly written. The identifier datum may further include certain data from the manufacturer, as such the identifier datum may include both the UID and certain manufacturer data.

The first circuit 124 may also include memory fields including various identification data that identifies the manifold with specificity. The manufacturing identification data includes such data as a model of the manifold, a serial number, an authorization code, and a lot number. For example, in one field, data indicating a use by date for the manifold is stored. In another field, the first circuit 124 may include vacuum level data. These data are used to establish the vacuum level (inmHg.) that the vacuum pump 110 should draw through the manifold 116.

The first circuit 124 may also include one or more randomized data set. The randomized data set may include at least one datum of the randomized data. One or more of the datums of the randomized data may be stored in separate memory field locations. One or more datums of the randomized data set may be stored in the first memory bank, the second memory bank, the third memory bank, or other memory bank different from the first memory bank, the second memory bank and so on. The first randomized data set may be stored in a first randomized data set field 212. The second randomized data set stored in a second randomized data set field 214 or may be utilized in RAM and not stored locally in one or more memory devices. The first randomized data set is typically different from the second randomized data set. While these are shown in different memory banks than the first and second memory banks, it is contemplated that the first and second memory banks could include those randomized data sets as mentioned above.

As described above, the first hash digest may be further based on one or more datums of the first randomized data set. The first hash digest may also be based on the one or more memory fields designating the number of manifold insertions permitted, the memory field designating a maximum volume allowed usage limit. In other words, the first hash digest may be based on the rover type, a value designating the number of manifold insertions permitted, the value designating the maximum volume allowed usage limit, or combinations thereof or other memory stored in the first memory bank.

The first hash digest may be created by utilizing a hash algorithm, such as SHA-1 hash algorithm, on the data sets described above to yield the first hash digest.

The second hash digest may also be based on one or more datums of the second randomized data set. The second hash digest may also be based on a number of manifold insertions performed, or a volume collected amount. In other words, the second hash digest may be based on the volume collected datum, the second randomized data set stored on the second memory bank, the number of insertions performed, a volume collected amount, or other data stored in the second memory banks. The second hash digest may be created by utilizing a hash algorithm, such as SHA-1 hash algorithm, on the data sets described above to yield the second hash digest. It is contemplated that the first and the second hash digests may be created using different hash algorithms. Advantageously, this approach ensures that the authentication signature will change if any byte of the first memory bank 200 and/or the second memory bank 202 changes.

Based on the underlying data that is inextricably linked to the first hash digest and the second hash digest, the first hash digest is different from the second hash digest. This first hash digest could be distinguished from the second hash digest in one or more ways, including but not limited to the length of the hash digest, the characters in the hash digest, or the sequence of the characters in the hash digest. This ensures that if one of two hash digests is compromised, the security of the underlying manifold is not fully-compromised. Other suitable hashing algorithms may be used, including but not limited to SHA-2, MD5, GOST, RIPEMD and/or SNEFRU algorithms.

The contents of the first memory bank 200 may be encrypted with a first key. The first key may be based on at least one datum of a randomized data set, such as one or more datums stored in the first randomized data set field 212, which is stored in a location other than the first memory bank. More particularly, in some instances, the first key may be based on a mathematical derivative of the datum or datums of the randomized data set generated by yet another hashing or XOR or obfuscation operation. The first key may be further based on an authentication key. The authentication key, also known as the static key, may be stored in various locations, such as a memory field of the programming station 154, a memory field of the first circuit 124, or a memory field of the waste collection unit 100. In one particular configuration, the authentication key may be located on the first circuit 124.

The contents of the first memory bank 200 may be mathematically combined, such as encrypted, with the first key to create a resulting bit string, the encrypted contents of the first memory bank (including, but not limited to the encrypted first hash digest). The first hash digest is generated using a suitable encryption algorithm, such as a SHA-1 algorithm which produces a 160-bit message digest.

The contents of the second memory bank 202 may be encrypted with a second key. The second key may be based on at least one datum of the second randomized data set. The second key may be based on a different randomized data set from the first key. In one configuration, the at least one datum of the second randomized data set is based on at least one datum of the first randomized data field, and/or a datum stored in the second randomized data set field 214, which is stored in a location other than the second memory bank. The contents of the second memory bank 202 may be encrypted with the second key to create a resulting bit string, the encrypted contents of the second memory bank (including, but not limited to the encrypted second hash digest). The first key, the second key, and/or the authentication key may each independently be an asymmetric key or a symmetric key.

The first key may be different from the second key in various ways such that if one of the first key and the second key is compromised, the security of the underlying manifold is not fully-compromised. The first key and the second key may each be independently generated by any suitable means, including without limitation, manual entry, noise sampling, pseudorandom number generation, or any combination thereof.

The encryption of the first memory bank and/or the second memory bank may be encrypted using different keys (as mentioned above), and with a different encryption process (i.e., using different encryption vector). The encryption vector may be generated based on any the data described above, such as one ore more datums of the randomized data sets, any or the contents of the first memory bank, the second first memory bank, and/or the identification datum.

The first hash digest and/or the second hash digest or encrypted forms thereof, may be used as authentication signatures to be read by the waste collection unit 100 to authenticate the manifold 116. It should be understood that other data present in the memory banks of the memory devices of the manifolds may also be used as part of the authentication signature, including but not limited to the rover type or the volume collected datum.

A second manifold 300 may be obtained in various ways. The second manifold 300 may be obtained by injection molding plastic or other material to form the second manifold that includes a second housing defining a surface, the housing defining a second manifold volume and a second outlet opening in fluid communication with the second manifold volume.

Alternatively, the second manifold 300 may be obtained by cleaning a used manifold that was used in a first procedure room 202 at a first medical facility 204 with a first waste collection unit 100. The second manifold 300 may be cleaned using an acceptable cleaning agent, such as a detergent, and cleaning techniques, such as using an ultrasonic bath. The second manifold 300 may be exposed to one or more sterilants. During the cleaning process, the drip stop seal may be removed, and when the cleaning process is completed, the drip stop seal may be reinserted into the outlet opening of the second manifold 300. The originally coupled circuit may be removed from the housing of the second manifold 300 so that a new circuit, i.e., the second circuit 308 may be installed in its place.

The used manifold may have one or more contaminants in the manifold volume. The method may include removing the one or more contaminants from the first manifold volume.

The method may further comprise further comprising overwriting a time stamp datum on the first memory device 128 of the used manifold. The time stamp datum could be in any of the memory banks described above, or in an alternative memory bank included on the memory device of the used manifold. In other words, in one specific embodiment, the time stamp datum is included in the first or second memory bank of the memory device of the used manifold.

Figure 6B:
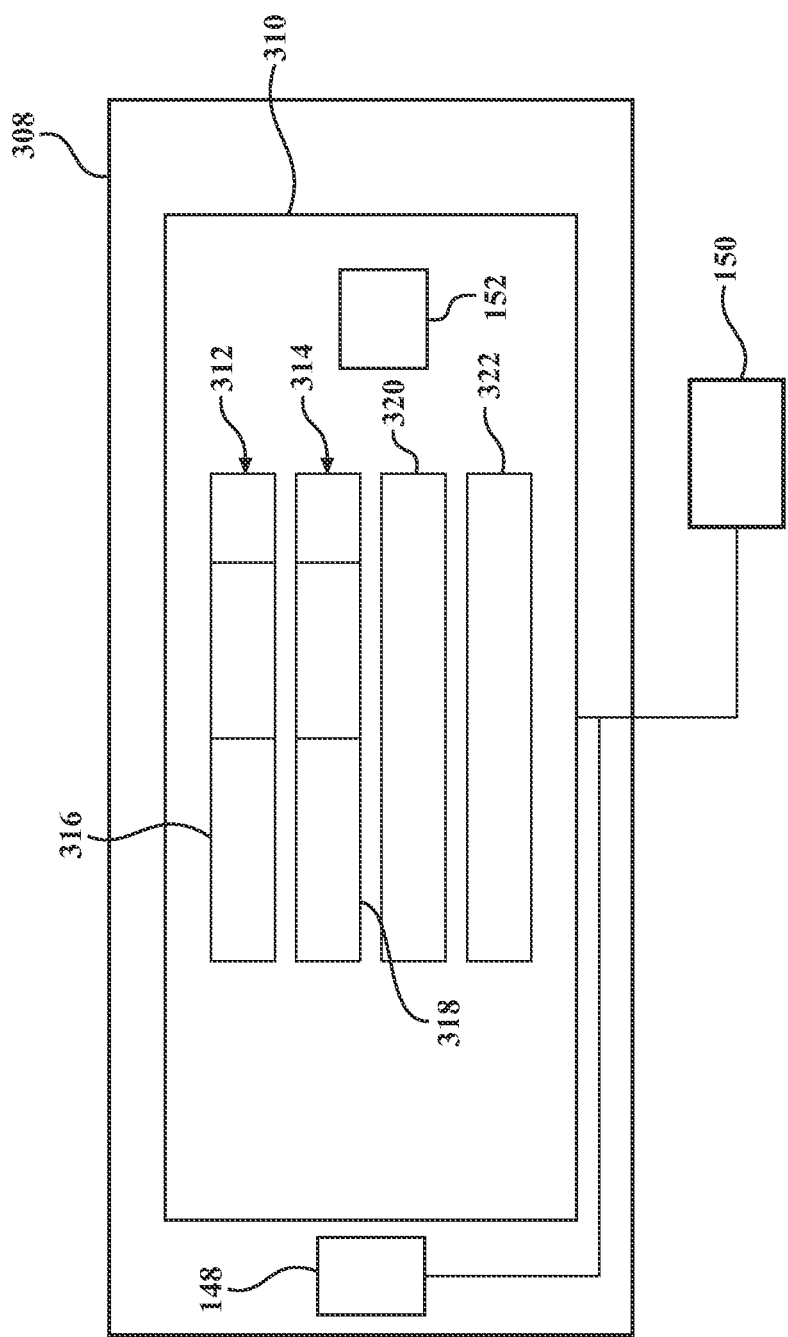
FIG. 6B is a schematic view of the second circuit configured for attachment to a manifold.

Referring to FIG. 6B, the method may include coupling a second circuit 308 (a new circuit) to a surface of the second manifold. The coupling of the second circuit may be performed using an adhesive or other fastening means. The second circuit 308 may include any of the hardware and/or data described above with respect to the first circuit 124. The second circuit 308 may comprise a second memory device 310. The second memory device 310 may be configured to include a third memory bank 312 and a fourth memory bank 314. The third memory bank 312 may include a fifth memory field 316 including the first hash digest based on the rover type and the fourth memory bank 314 including a sixth memory field 318 including the second hash digest based on the volume collected datum. As described below, the fifth memory field may include the encrypted first hash digest and the sixth memory field may include the encrypted second hash digest.

The second circuit 308 may be configured to produce a contamination signal in response to receiving a contamination status command signal from the waste collection unit to which it is received. As described above, the contamination command signal may be sent by the controller 120 based on a determination by the controller 120 as to whether there has been vacuum pressure in the manifold by monitoring whether or not the vacuum pump 110 was turned on and was set at a non-zero vacuum setting. In such instances, the second circuit 308 may include a processor capable of producing a contamination signal in response to receipt of a contamination command signal. Alternatively, the second circuit 308 may be programmed to set a contamination bit in response to receiving a contamination command signal.

It should be appreciated that the fifth memory field 316 may include the exact same contents as the second memory field 206 described above for the memory device 128. Similarly, the sixth memory field 318 may include the exact same contents as the fourth memory field 210 described above for the memory device 128. The second memory device 310 may also include the same identification datum as the first memory device 128 despite the fact that the identification datum may be promised as truly unique in the world.

Similar to what is described with respect to the first memory bank, the contents of the third memory bank 312 may be encrypted with the first key. The first key may be based on at least one datum of a randomized data set, such as one or more datums stored in the third randomized data set field 320, or be derived from the first randomized data set field. The first key may be further based on the authentication key. The contents of the third memory bank 312 may be encrypted with the first key to create a resulting bit string, the encrypted contents of the third memory bank (including, but not limited to, the encrypted first hash digest). Similar to what is described with respect to the second memory bank, the fourth memory bank 314 may be encrypted with the second key. The second key may be based on a randomized data set. In one configuration, the second key is based on a datum stored in a fourth randomized data set field 322 or other data set field. The contents of the fourth memory bank 314 may be encrypted with the second key to create a resulting bit string, the encrypted contents of the fourth memory bank (including the encrypted second hash digest).

The second memory device 310 may include the exact same characters in third randomized data set field and its fourth randomized data set field as the characters stored in the first randomized data set field and the second randomized data set field. Or, they may be different.

The method may include selling and/or shipping the second manifold to a different healthcare facility and/or different procedure room than the healthcare facility and/or procedure room from which the first manifold was obtained. This ensures that the waste collection unit assigned to the healthcare facility/procedure room that will ultimately utilize the second manifold has no record of the identification datum present on the second circuit being utilized with that particular vacuum pump.

Healthcare facility can mean any building or structure that includes personnel providing one or more medical treatment. Suitable exemplary healthcare facilities include hospitals, gastroenterology centers, urgent care facilities, doctor's offices, or the like.

The method may further include obtaining a third manifold 400. The third manifold may include a third housing defining a surface, a third manifold volume, and a third outlet opening in fluid communication with the third manifold volume. The third manifold 400 may be injection molded or may be obtained by cleaning a used manifold with a used circuit as described with respect to how the second manifold may be obtained.

Figure 7:
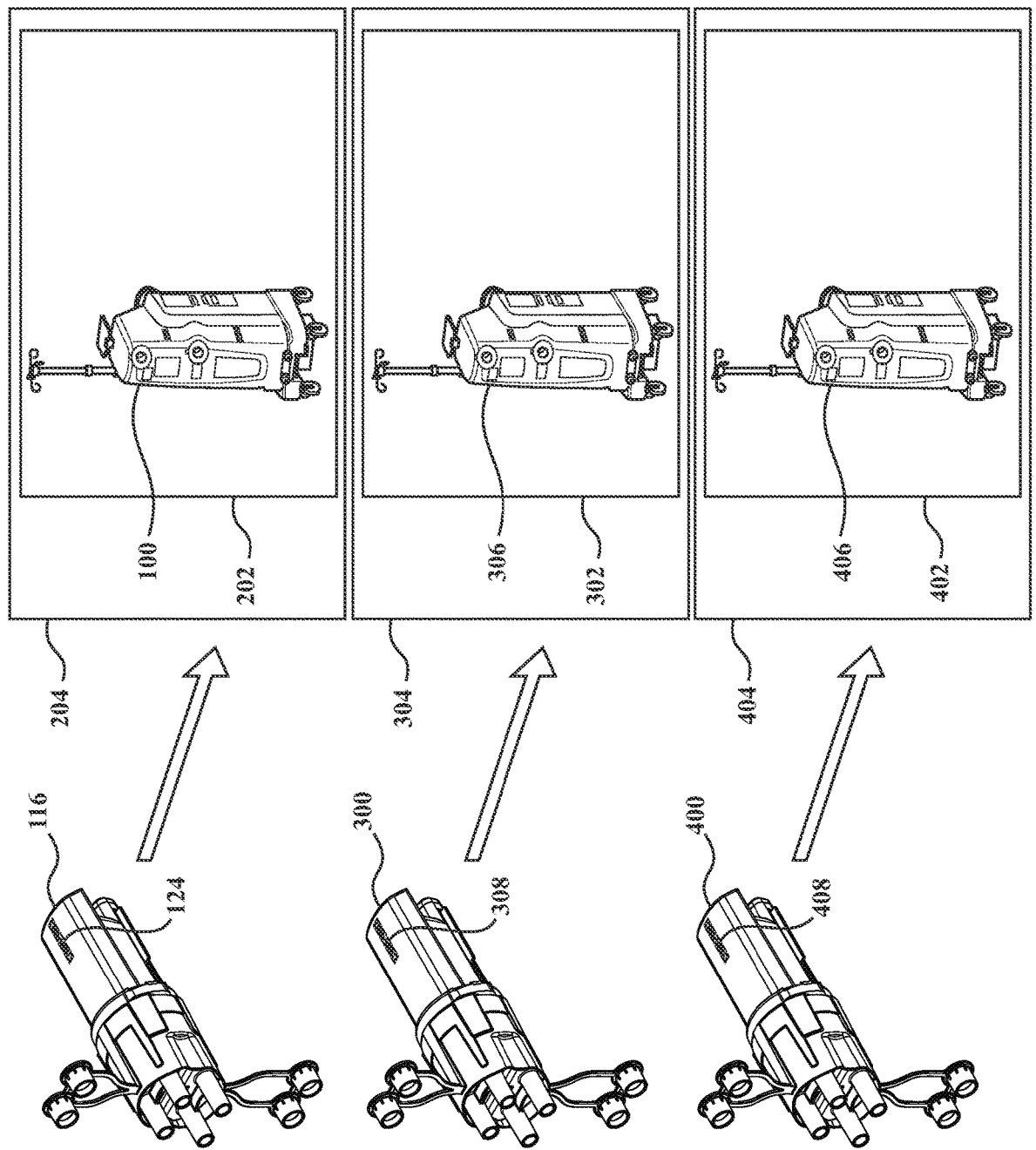
FIG. 7 is a schematic diagram showing a potential distribution system for the surgical waste manifolds.
Figure 8B:
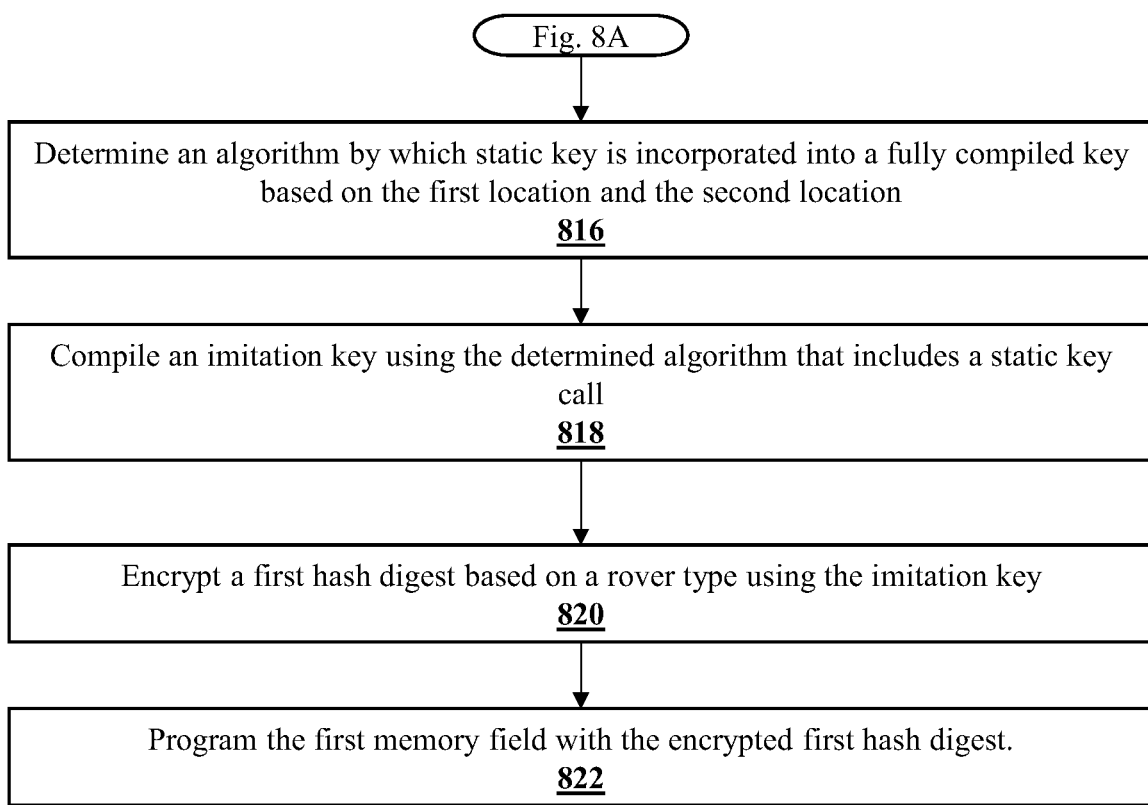
Figure 10:
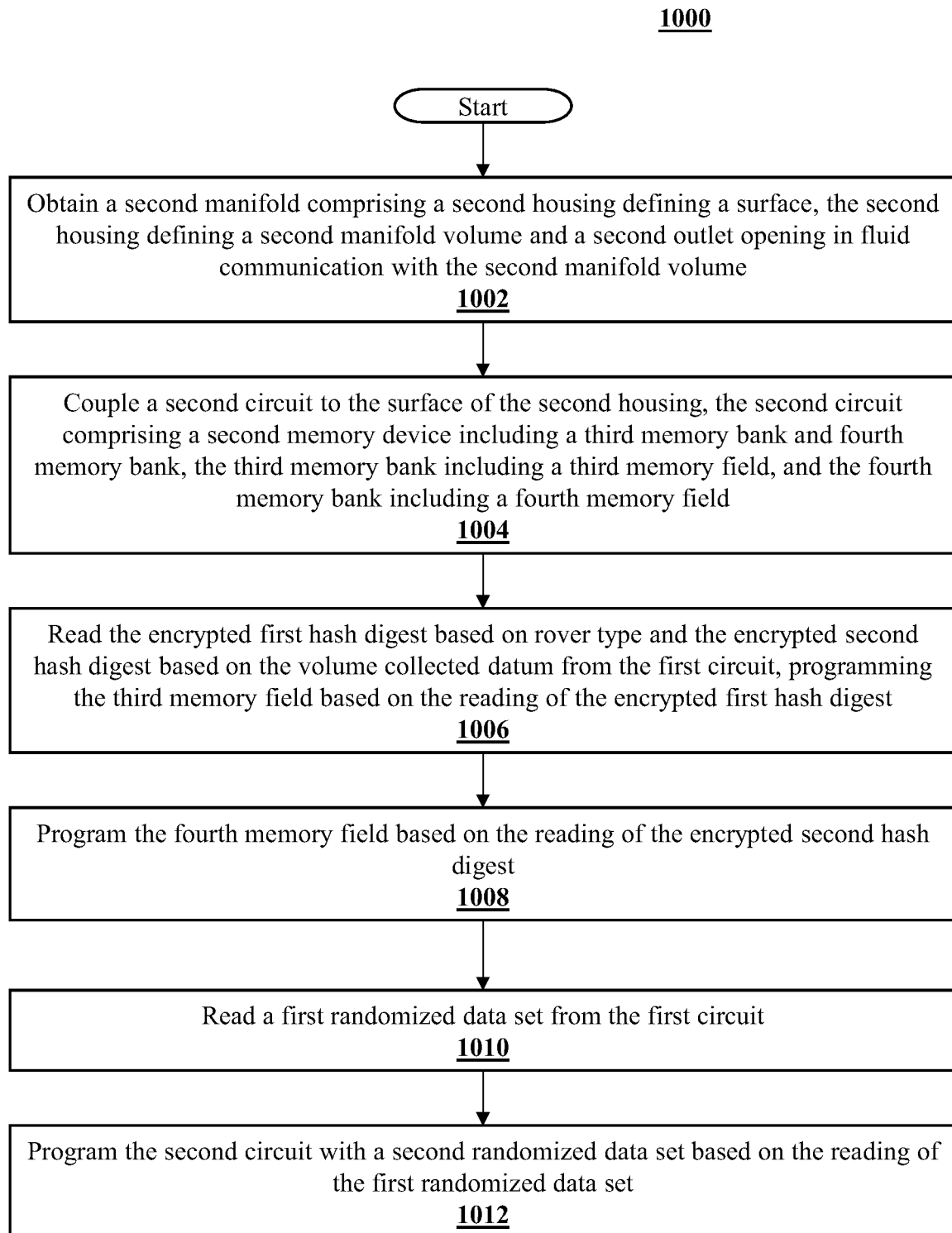
FIG. 10 is a flow chart depicting yet another exemplary method.

Referring to FIG. 7, the method may include shipping and/or selling the third manifold 400 to a third procedure room 402 at a third medical facility 404 having a second surgical waste collection unit 406 where the second medical facility 304 is located in a different location than the third medical facility 404 and the first medical facility 204. This could be a different address, a different state, a different country, a different city, etc. Alternatively, the method may include selling and/or shipping the second manifold and the third manifold to two different procedure rooms in the same healthcare facility.

Figure 6C:
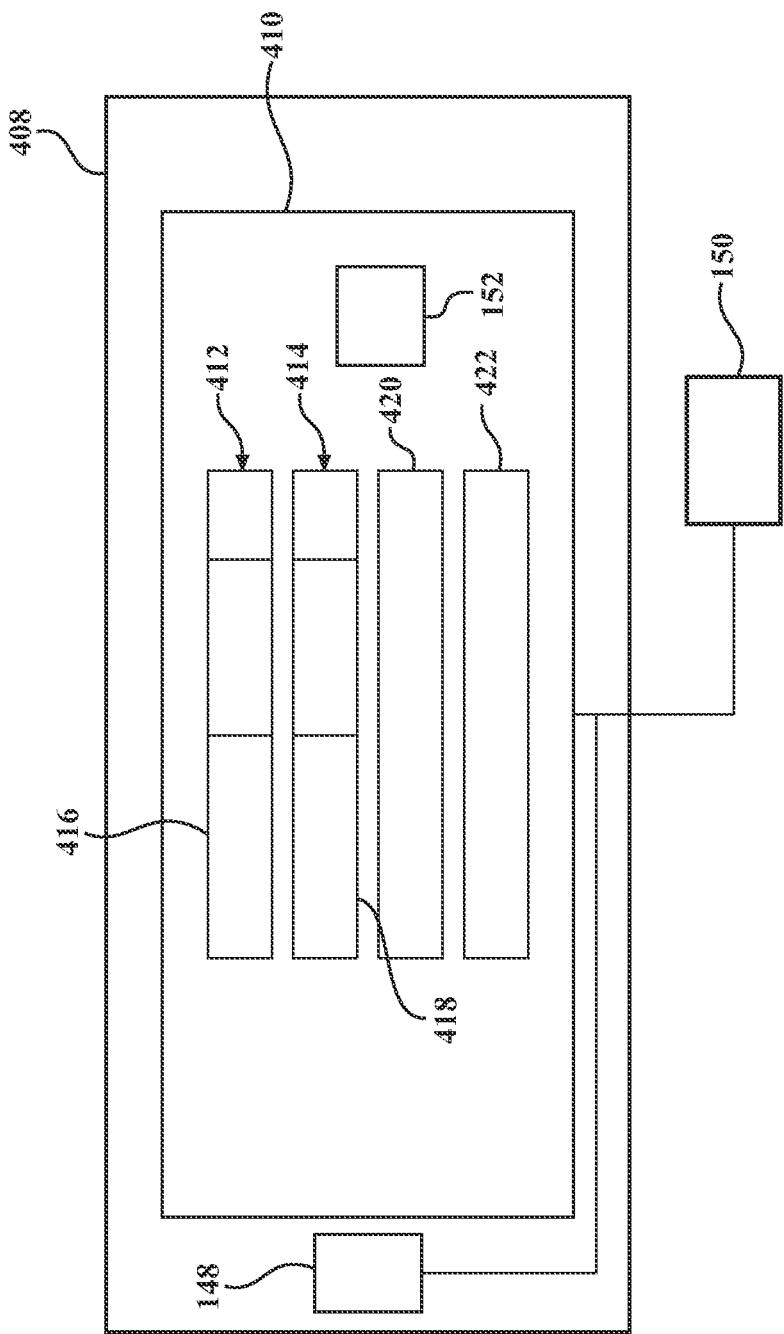
FIG. 6C is a schematic view of the third circuit of FIG. 2 configured for attachment to a manifold.

Referring to FIG. 6C, the method may include coupling a third circuit 408 to the surface of the third manifold 400, the third circuit comprising a third memory device 408 including a fifth memory bank 412 and a sixth memory bank 414, the fifth memory bank 412 including a seventh memory field 416 including the first hash digest based on the rover type, the sixth memory bank 414 including an eighth memory field 418 including the second hash digest based on the volume collected datum.

The third circuit 408 may be configured to produce a contamination signal in response to receiving a contamination status command signal from the waste collection unit to which it is received. As described above, the contamination command signal may be sent by the controller 120 based a determination by the controller 120 as to whether there has been vacuum pressure in the manifold by monitoring whether or not the vacuum pump 110 was turned on and was set at a non-zero vacuum setting. In such instances, the third circuit may include a processor capable of producing a contamination signal in response to receiving a contamination signal. Alternatively, the third circuit 408 may be programmed to set a contamination bit in response to receiving a contamination command signal.

It should be appreciated that the seventh memory field 416 may include the exact same contents as the fifth memory field 316 described above for the second memory device 310. Similarly, the eighth memory field 418 may include the exact same contents as the sixth memory field 318 described above for the second memory device 310. The third memory device 410 may also include the same identification datum as the second memory device 310.

The contents of the fifth memory bank 412 may be encrypted with the first key. The first key may be based on at least one datum of a randomized data set, such as one or more datums stored in the fifth randomized data set field 420 or other datums in other randomized data set fields. The first key may be further based on the authentication key. The contents of the fifth memory bank 412 may be encrypted with the first key to create a resulting bit string, the encrypted contents of the fifth memory bank (the first hash digest).

The contents of the sixth memory bank 414 may be encrypted with the second key. The second key may be based on at least one datum of a randomized data set. In one configuration, the second key is based on a datum stored in a sixth randomized data set field 422 or a derivative of some other randomized data set field. The contents of the sixth memory bank 414 may be encrypted with the second key to create a resulting bit string, the encrypted contents of the fourth memory bank (including but not limited to the encrypted second hash digest).

The third memory device 410 may include the exact same characters in fifth randomized data set field and its sixth randomized data set field as the characters stored in the third randomized data set field and the fourth randomized data set field of the second memory device 310, and optionally the same as the characters stored in the first randomized data set field and the second randomized data set field of the first memory device 128.

The first memory device 128, the second memory device 310, and the third memory device 410 may also include the same UID.

The method may also include reading the identification datum from the memory device of the first manifold, and replicating that identification datum on the memory device of the second manifold, third manifold, etc.

In some configurations, at least one datum of the at least one randomized data set of the second circuit is the same as at least one datum of at least one randomized data set of the third circuit.

It should be appreciated that while the third memory device 310 and the second memory device 410 may include much of the exact data, the third memory device 310 need not be a complete replica of the second memory device 410.

The method may further include reading the contents of a new manifold including the first circuit described above before the new manifold has been inserted into any waste collection unit. More particularly, the method may further include reading the contents of the first circuit of the new manifold including the first circuit before any contaminants have entered into the manifold volume of that new manifold. The contents read from the first circuit of the new manifold may be copied to the second circuit of the second manifold and to the third circuit of the third manifold as described above.

The method may include reading the first hash digest based on rover type from the first circuit and the second hash digest based on the volume collected datum and programming the third memory field based on the reading of the first hash digest. The method may also include programming the fourth memory field based on the reading of the second hash digest and reading a first randomized data set from the first circuit. The method may also include programming the second circuit with a second randomized data set based on the reading of the first randomized data set. In some instances, the second circuit may be programmed with an exact copy of data read from the first circuit, such as an exact copy of the first randomized data set, the first hash digest and the second hash digest. The first and the second hash digests may be the unencrypted or encrypted form during this step of reading and/or the step of programming.

In certain instances, the method may include reading contents of a used manifold including the first circuit described above after the manifold has been inserted into a waste collection unit and after one or more contaminants have entered into the manifold volume of the unused manifold. The method may further comprise overwriting a time of first use on the first memory device 128 of the used first manifold. The method may further include overwriting one or more memory fields of the first circuit with a rover type, an encrypted or unencrypted hash digest based on the rover type, a volume collected datum, and/or an encrypted or unencrypted hash digest based on the volume collected datum. In other words, the used manifold will include certain information on the circuit of that manifold, and the method may include overwriting that certain information. For example, the method may include programming the second memory field of the used first manifold with a third hash digest, the third hash digest different from the first hash digest and being based on the rover type and programming the fourth memory field of the used first manifold with a fourth hash digest, the fourth hash digest different from the second hash digest and being based on the rover type. The method may also include programming the time stamp field on the first memory device 128 indicating that no first use has occurred. This may include overwriting the time stamp field where the time of first use was initially written.

It should be appreciated that throughout this disclosure in instances where the hash digest(s) are mentioned, it is contemplated that the encrypted form of the hash digest may be substituted for the unencrypted form of the hash digest. For example, in instances where this description describes programming a first hash digest, it is also contemplated that the method may include programming an encrypted form of the first hash digest. This is contemplated for both the first and second hash digests described throughout.

In certain instances, the used first manifold may have been obtained from a first procedure room 204 having a first surgical waste collection rover 100. In those instances, the method further comprises shipping the cleaned first manifold to a second procedure room 304 having a second surgical waste collection rover 306, the second surgical waste collection rover 306 having different memory contents than the first surgical waste collection rover 100.

Contaminants as used herein can mean any type of tissue or bodily fluid.

A method of harvesting an authentication procedure from a waste collection unit 100 for surgical waste or other medical device is described below. In such an instance, the waste collection unit 100 may include a reader 122 disposed adjacent the receiver 112. The waste collection unit 100 may include a reader controller (123) coupled to the reader 122 and a second controller 120 coupled to the reader controller 120 and the vacuum pump 110. The waste collection unit may include a waste collection unit memory device (121), which may be in communication with the second controller 120.

In such a method, a manifold 116 is obtained or manufactured as described above. The manifold may include the structure features described above, including the housing and outlet opening. The manifold may further include a circuit 124 coupled to the housing. The circuit 124 may include the memory device 128 that includes a first memory bank and a second memory bank as described above. The first memory bank including a first memory field and a second memory field. The second memory bank including a third memory field and a fourth memory field. The circuit 124 may be coupled to the housing before or after programming, and/or during programming. In other words, it is contemplated that at least one memory field of the memory device 128 may be programmed before the memory device 128 is coupled to the housing of the manifold and that at least one additional memory field of the memory device 128 may be programmed after the memory device 128 is coupled to the housing.

The method may include a step extracting object code from the waste collection unit memory device 121. This may include extracting portions of object code from object modules or executables stored on the waste collection unit memory device 121. This may include extracting object code from the waste collection unit memory device 121 related to an authentication executable. This authentication executable may contain function calls utilized to authenticate genuine manifolds. In order to extract the object code, a secondary computer, typically including a processor and memory, is at least placed in temporary communication with reader controller 123, the second controller 120, and/or the waste collection unit memory device 121. By placing the secondary computer in communication with these components, the user may copy extracted object code to a memory device associated with the secondary computer or the user may be view the object code via the secondary computer, while the object code remains on the one or more components of the waste collection unit.

Once the object code has been extracted from the waste collection unit, the method may include the step of disassembling at least a portion of the extracted object code into a human-comprehensible form having a different convention from the object code. The disassembly process may include converting the extracted object code into assembler language statements that can be assembled to generate a replica of the original source code. The step of disassembly may further include identifying portions of the object code as data only, instructions only, a combination of data and instructions. The step of disassembling may be facilitated using a disassembly utility, such IDA Pro or Relyze. Once the object code has been disassembled and organized, the object code is understood to be disassembled into the human-comprehensible form.

The human-comprehensible form of the extracted object code is then analyzed to identify one or more calls to specific data at specific locations. In one potential implementation, the human-comprehensible form of the object code is analyzed to identify an authentication executable. The authentication executable may be further analyzed to identify one or more calls to one or more keys within the instructions present in the authentication executable. These cases may be function calls in instances where one or more static keys (described as the first key and second key above) and one or more fully compiled keys are stored in flash memory on the waste collection unit.

The method may further include identifying a location of a fully compiled key call within the comprehensible form of the object code. The fully compiled key may be utilized to encrypt one or more memory banks of the memory device 128. The fully compiled key may be stored in the memory device 128. Alternatively, the fully compiled key may be stored in the waste collection unit memory device 121. The fully compiled key may be ultimately used to encrypt one or more portions of the memory device 128 of the manifold such that the waste collection unit would perceive the manifold as genuine.

The method may also include identification of a static key call within the comprehensible form of the object code. The static key may vary across a single lot of manifolds or the static key may change every week, month, year, etc. of manufacture. The static key may be stored on the memory device 128 coupled to the manifold. In other words, the memory device 128 of every circuit coupled to every manifold may include the same static key. The static key may be stored in a secure portion of the memory device 128. The secure portion of the memory device 128 may be a discrete memory location(s) that is password protected or encrypted, through software or hardware mechanisms. Alternatively, the static key may be stored on the waste collection unit memory device 121. Again, this waste collection unit memory device 121 may include a secure portion as described above with respect to the memory device 128. The static key may also be stored in other hardware of the waste collection unit, such as within in a secure portion within the second controller 120 of the waste collection unit. Alternatively still, the static key may be located on a remote server that is in communication with the waste collection unit. The identification of the static key call may include identifying the location of the static key call. The step of identification may include a determination that the location of the static key call is in the waste collection unit memory device 121. Alternatively, the location of the static key may be on the memory device 128 of the circuit of the manifold.

In certain optional implementations, the static key may include one or more static key components, including a first static key component and a second static key component. In such an implementation, the method may include identification of a first static key component call and a second static key component call. Subsequently, the method may include determining a location of the first static key component and the second static key component. The first static key component may be located in a different location than the second static key component. This may include different memory fields within the same component, e.g., different memory fields in the waste collection memory device 121, or may be located in different components, i.e., the first static key component may be located in the waste collection unit memory device 121 and the second static key component may be located on the memory device 128. Of course, it is contemplated that the first static key component and/or the second static key component may be located in other components, such as in the second controller 120 of the waste collection unit and the second static key component may be located in the waste collection unit memory device 121. It is also contemplated that the method may including identification of more than two static key components. Because the static key (or one or more static key components) may be stored in a secure portion of the waste collection unit memory device 121 or the memory device 128, the method may further include decryption of the secure portion of the respective memory device 121, 128 before identifying the static key call (or the first and second static key component).

Once the locations for the fully compiled key and the locations for the static key have been identified, the method may include determining the algorithm by which the static key is incorporated into the fully compiled key based on the location of the static key and the location of the fully compiled key. This step may include determining how various data is encrypted together with the static key (or static key components). The method may include determining a sequence of algorithmic steps used to generate a genuine authentic key. For example, the step of determining the sequence of algorithmic steps may include determining that an XOR operation precedes incorporation of random data. The step of determining the algorithm may include determine a sequence of a first data component and a second data component of the genuine authentication key. The method may also include identifying a first data component call for the first data component and identifying a second data component call for the second component of the algorithm. Based on the first data component call and the second data component call, the method may further involve determining a location of the first data component and determining a location of the second data component. The first data component and the second data component may be based on at least one datum of the randomized data set described above, and hence the location of the first data component and/or the second data component may be on the memory device 128. However, it is also contemplated that the first data component and/or the second data component may be stored on the waste collection unit memory device 121. The determination of the algorithm may be facilitated by one or more side channel attacks. This may include the monitoring the time by which the second controller performs various operations, or by determining the pattern and/or length of various messages sent by the second controller 120. The ultimate result of determination of the algorithm based on the locations of the fully compiled key and the static key (or components thereof) includes the sequence and process of combining various data segments to generate the fully compiled key.

Based on the determination of the algorithm, the method may include the further step of compiling an imitation key using the determined algorithm. The compilation of the imitation key may include compiling the static key (or components thereof) with various other data components, such as the first data component and the second data component. It is further contemplated that the imitation key may be compiled based on other data components stored on the memory device 128 or based on data components stored on the waste collection unit memory device 121.

The method may include encrypting the first memory bank of the memory device 128 using the imitation key after programming the first memory field with a rover type and a second memory field with a first hash digest based on the rover type. The method may also include encrypting the second memory bank using the imitation key after the step of programming the third memory field with a volume collected datum and the fourth memory field with a second hash digest based on the volume collected datum. In certain implementations, the method may further include identifying a fully compiled second key call within the comprehensible form of object code in a similar fashion as described above with a first fully compiled key call. This includes identifying a location for the fully compiled second key call, and determining a second algorithm by which the static key is incorporated into a fully compiled second key based on the location of the second fully compiled key and the location of the static key described above. In addition, such a method would include compiling a second imitation key using the determined second algorithm that includes the static key call and encrypting a second memory bank of the memory device 128 using the second imitation key. In certain instances, just the hash digest based on the rover type is encrypted. Alternatively, the other contents of the memory bank that includes the memory field including the rover type may also be encrypted along with the first hash digest. Similarly, the hash digest based on the volume collected datum may be encrypted, and/or the hash digest based on the volume collected datum in combination with the other contents of the memory bank that includes the memory field including the volume collected datum. The location of the calls for the second fully compiled second key and the first fully compiled key may be the same.

In this application, including the definitions below, the term "controller" may be replaced with the term "circuit", and vice-versa. The term "controller" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The controller may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The controller may communicate with other controllers using the interface circuit(s). Although the controller may be depicted in the present disclosure as logically communicating directly with other controllers, in various configurations the controller may actually communicate via a communications system. The communications system includes physical and/or virtual networking equipment such as hubs, switches, routers, and gateways. In some configurations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various configurations, the functionality of the controller may be distributed among multiple controllers that are connected via the communications system. For example, multiple controllers may implement the same functionality distributed by a load balancing system. In a further example, the functionality of the controller may be split between a server (also known as remote, or cloud) controller and a client (or, user) controller.

Some or all hardware features of a controller may be defined using a language for hardware description, such as IEEE Standard 1364-2005 (commonly called "Verilog") and IEEE Standard 10182-2008 (commonly called "VHDL"). The hardware description language may be used to manufacture and/or program a hardware circuit. In some configurations, some or all features of a controller may be defined by a language, such as IEEE 1666-2005 (commonly called "System C"), that encompasses both code, as described below, and hardware description.

The term code, as used above, may include software, firmware, and/or microcode, and may refer to programs, routines, functions, classes, data structures, and/or objects. The term shared processor circuit encompasses a single processor circuit that executes some or all code from multiple controllers. The term group processor circuit encompasses a processor circuit that, in combination with additional processor circuits, executes some or all code from one or more controllers. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple controllers. The term group memory circuit encompasses a memory circuit that, in combination with additional memories, stores some or all code from one or more controllers.

The term memory device is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general-purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Swift, Haskell, Go, SQL, R, Lisp, Java®, Fortran, Perl, Pascal, Curl, OCaml, JavaScript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SENSORLINK, and Python®.

The foregoing description is not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A method of harvesting an authentication procedure from a surgical waste collection unit, the surgical waste collection unit including a first container for holding medical waste, a vacuum pump in fluid communication with the first container, the vacuum pump configured to draw a vacuum on the first container, a receiver adjacent the first container, the receiver dimensioned to receive a manifold housing, a reader disposed adjacent the receiver, a first controller coupled to the reader and a second controller coupled to the first controller and the vacuum pump, the second controller comprising a first memory device, said method comprising:
   obtaining a first manifold comprising a first housing defining a surface, the first housing defining a first manifold volume and a first outlet opening in fluid communication with the first manifold volume;
   coupling a first circuit to the surface of the first housing, the first circuit comprising a second memory device including a first memory bank, the first memory bank including a first memory field and a second memory field;
   extracting object code related to an authentication executable from the first memory device;
   disassembling at least a portion of the extracted object code into a comprehensible form having a different convention from the object code;
   identifying a fully compiled key call within the comprehensible form;
   identifying a static key call within the comprehensible form;
   identifying a first location for the fully compiled key call and a second location for the static key call;
   determining an algorithm by which static key is incorporated into a fully compiled key based on the first location and the second location;
   compiling an imitation key using the determined algorithm that includes a static key call;
   encrypting a first hash digest based on a rover type stored in the second memory field using the imitation key; and
   programming the first memory field with the encrypted first hash digest as an authentication signature to be read by the surgical waste collection unit to authenticate the first manifold.

2. The method of claim 1, wherein the step of identifying the second location for the static key call is further defined as identifying the second location on the second memory device.

3. The method of claim 1, wherein the step of identifying the second location for the static key call is further defined as identifying the second location on the first memory device.

4. The method of claim 1, wherein the step of determining the algorithm includes determining a sequence of algorithmic steps used to generate a genuine authentication key based on the identified first location and the identified second location.

5. The method of claim 4, wherein the step of determining the algorithm includes determining a sequence of a first data component and a second data component in the genuine authentication key based on a location of a call for the first data component and based on a location of a call for the second data component.

6. The method of claim 5, wherein the step of determining the algorithm includes determining that the location for the first data component is a location on the second memory device.

7. The method of claim 5, wherein the step of encrypting the first hash digest is further defined as encrypting the first hash digest and the first memory bank using the imitation key, and wherein the rover type is stored in the first memory field.

8. The method of claim 1, wherein the step of identifying the first location for the fully compiled key call is further defined as identifying that the first location for the fully compiled key call is a location on the first memory device.

9. The method of claim 1, wherein the step of identifying the first location for the fully compiled key call is further defined as identifying that the first location for the fully compiled key call is a location on the second memory device.

10. The method of claim 1, wherein the second memory device further comprises a second memory bank, the second memory bank including a third memory field and a fourth memory field, the method further, identifying a third location for the fully compiled second key call, and determining a second algorithm by which the static key is incorporated into a fully compiled second key based on the second location and the third location, and compiling a second imitation key using the determined second algorithm that includes the static key call; and
   encrypting a second hash digest based on the volume collected datum using the second imitation key; and
   programming the third memory field of the second memory bank with the encrypted second hash digest.

* * * * *